US008944102B1

(12) United States Patent
Wiederin et al.

(10) Patent No.: US 8,944,102 B1
(45) Date of Patent: Feb. 3, 2015

(54) GAS BURST INJECTION VALVE

(75) Inventors: Daniel R. Wiederin, Omaha, NE (US); Nathan Saetveit, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 415 days.

(21) Appl. No.: 13/414,210

(22) Filed: Mar. 7, 2012

Related U.S. Application Data

(60) Provisional application No. 61/450,036, filed on Mar. 7, 2011.

(51) Int. Cl.

| | |
|---|---|
| ***F16K 11/074*** | (2006.01) |
| ***G01N 1/00*** | (2006.01) |
| ***G01N 30/20*** | (2006.01) |

(52) U.S. Cl.
USPC ................... 137/625.46; 73/863.73; 73/61.56

(58) Field of Classification Search
USPC ........ 137/625.46; 73/863.72, 863.73, 863.74, 73/61.55, 61.56
See application file for complete search history.

(56) References Cited

U.S. PATENT DOCUMENTS

| | | | | |
|---|---|---|---|---|
| 4,729,876 | A * | 3/1988 | Hennessy et al. | 422/539 |
| 4,926,702 | A * | 5/1990 | Stephens et al. | 73/864.83 |
| 5,255,568 | A * | 10/1993 | del Valle et al. | 73/863.73 |
| 6,382,035 | B1 * | 5/2002 | Nichols | 73/863.72 |
| 6,672,336 | B2 * | 1/2004 | Nichols | 137/625.46 |
| 6,874,354 | B2 * | 4/2005 | Cueni et al. | 73/61.55 |
| 8,286,663 | B2 * | 10/2012 | Kallback et al. | 137/625.15 |
| 8,322,197 | B2 * | 12/2012 | Koster et al. | 73/61.55 |

* cited by examiner

*Primary Examiner* — John Fox
(74) *Attorney, Agent, or Firm* — Advent, LLP

(57) ABSTRACT

Valve assemblies are described that provide bursts of gas between fluids to furnish separation between the fluids. A valve assembly includes a first valve member having ports configured to connect to an external loop, an output, and a vent, and ports configured to receive a first fluid, a second fluid, and a pressurized gas. The valve assembly further includes a second valve member coupled adjacent the first valve member having channels configured to connect the external loop to the second fluid for charging the external loop with the second fluid, and to connect the external loop to the output for supplying the second fluid from the external loop to the output. The second valve member also has one or more channels for receiving a burst of the pressurized gas via a port of the first valve member and supplying the pressurized gas to the output and/or to the external loop.

20 Claims, 10 Drawing Sheets

GAS BURST INJECTION VALVE

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Valve assemblies are described that provide one or more bursts (e.g., bubbles) of gas between fluids supplied to equipment connected thereto. The valve assemblies can furnish separation between two fluids (e.g., a sample fluid and a carrier fluid) supplied to instrumentation, such as ICP spectrometry instrumentation, and so forth. The valve assembly includes a first valve member (e.g., a stator) having ports configured to connect to an external loop (e.g., a sample loop), an output (e.g., a nebulizer, a column, and so forth), and a vent (e.g., waste). The first valve member also has ports configured to receive a first fluid (e.g., a carrier fluid), a second fluid (e.g., a sample fluid), and a pressurized gas. The valve assembly further includes a second valve member (e.g., a rotor) coupled adjacent to the first valve member and having channels configured to connect the external loop to the second fluid in one orientation (e.g., rotational position) for charging the external loop with the second fluid, and to connect the external loop to the output in another orientation (e.g., rotational position) for supplying the second fluid from the external loop to the output. The second valve member also has one or more channels for receiving a burst of the pressurized gas via a port of the first valve member and supplying the pressurized gas to the output and/or to the external loop.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

Figure 7:
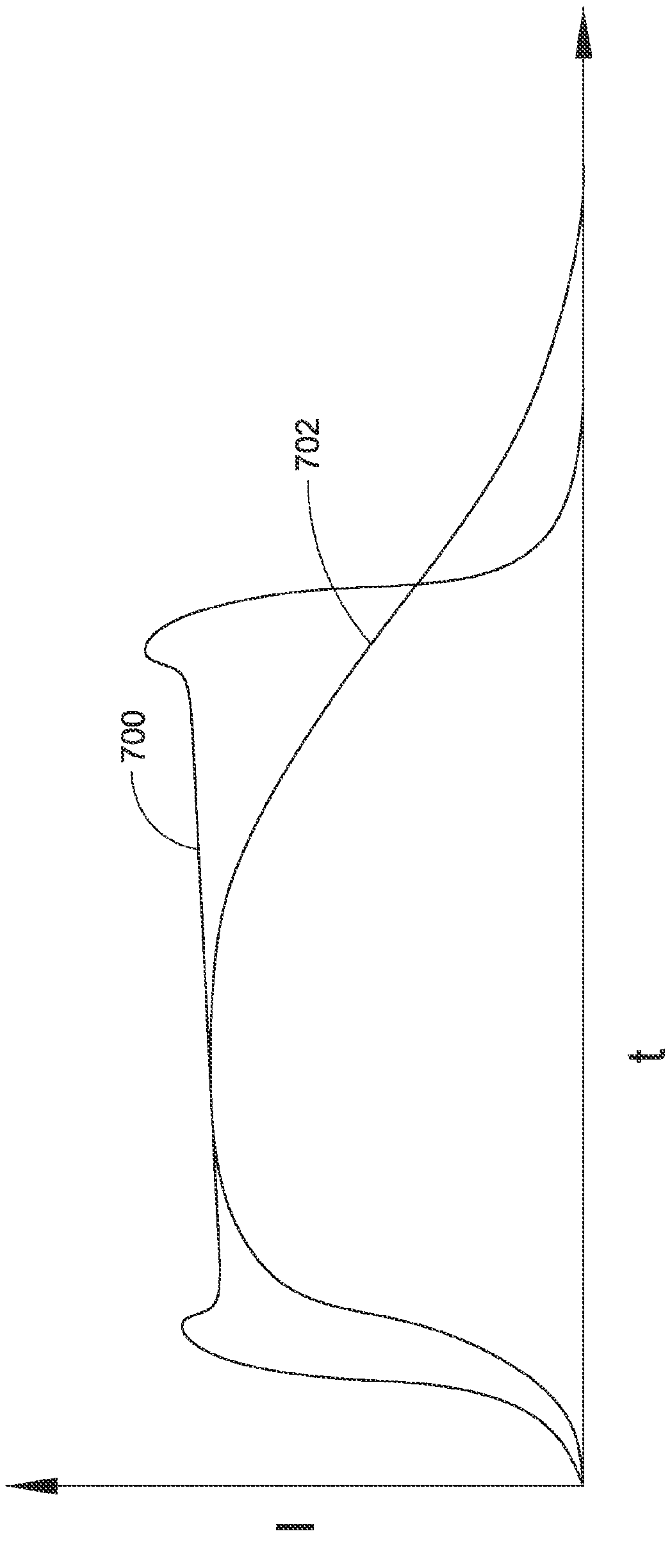

FIG. 7 is a graph illustrating signal intensity versus time for one signal representing the detection of a material performed via spectroscopic analysis using a multiport flow valve with a center bypass port configured to provide a half-way burst of gas in accordance with example implementations of the present disclosure, and for another signal representing the detection of a material performed via spectroscopic analysis using a multiport flow valve without providing a half-way burst of gas.

DETAILED DESCRIPTION

Overview

Multiport valves are typically used to transport sample materials to laboratory equipment for analysis. For example, multiport valves can be used to introduce liquid samples into ICP spectrometry instrumentation for analysis. Multiport valves can also be used to load samples on columns for liquid and/or gas chromatography. Typical valves used in these applications include six-port (6-port), two-position (2-position) rotary valves. Generally, two ports of a rotary valve are connected to an external (sample) loop, one port is connected to a sample source, another port is connected to a carrier source, a further port is connected to a vent (waste), and another port is connected to a nebulizer/column. When the valve is in a first orientation, sample from the sample source flows through the sample loop, while carrier from the carrier source flows directly to a nebulizer/column. When the valve is rotated to a second orientation, the carrier source is connected to the sample loop for injecting the sample contained in the sample loop into the nebulizer or onto the column.

However, this valve configuration does not provide separation between sample and carrier, which can cause the resulting signals from analysis equipment to have instability for some time ahead of a measurable (e.g., stable) signal condition, and some time behind a measurable signal condition. This instability can make it difficult to measure/resolve the signal during these time intervals (e.g., as opposed to when the sample is flowing to the equipment unmixed with the carrier). Thus, such equipment generally requires that the sample is provided to the analysis equipment for a longer time, increasing both the amount of time necessary to measure the resulting signal, and the quantity of the sample needed for each measurement.

Accordingly, valve assemblies are described that provide one or more bursts (e.g., bubbles) of gas between fluids supplied to equipment connected thereto. A valve assembly configured in accordance with the present disclosure can furnish separation between two fluids (e.g., a sample fluid and a carrier fluid) supplied to instrumentation, such as ICP spectrometry instrumentation, and so forth. The valve assembly includes a first valve member (e.g., a stator) having ports configured to connect to an external loop (e.g., a sample loop), an output (e.g., a nebulizer, a column, and so forth), and a vent (e.g., waste). The first valve member also has ports configured to receive a first fluid (e.g., a carrier fluid), a second fluid (e.g., a sample fluid), and a third fluid (e.g., a pressurized gas). The valve assembly further includes a second valve member (e.g., a rotor) coupled adjacent to the first valve member and having channels configured to connect the external loop to the second fluid in one orientation (e.g., rotational position) for charging the external loop with the second fluid, and to connect the external loop to the output in another orientation (e.g., rotational position) for supplying the second fluid from the external loop to the output.

The second valve member also has one or more channels (e.g., pressure pockets) for receiving the pressurized gas via a port of the first valve member and supplying the pressurized gas to the output and/or to the external loop (e.g., without directly connecting the source of the pressurized gas to the output and/or the external loop). In this manner, pressurized gas can be transferred indirectly via the pressure pockets from a pressurized gas source to the output and/or to the external loop. Thus, the size of the gas bursts/bubbles in a sample stream can be limited by the size of the pressure pockets, allowing very small bubbles (e.g., having a volume of less than one microliter (1 μL), for instance) to be injected into a sample stream in a reproducible manner. This can provide separation between the sample and the carrier without supplying a large burst of gas, which may otherwise result in plasma instability with, for example, spectrometry implementations (e.g., possibly extinguishing the plasma of an ICP plasma torch). However, it should be noted that in other implementations in accordance with the present disclosure, a source of pressurized gas may be connected directly to the sample stream via the one or more channels in the second valve member. In this type of implementation, the amount of pressurized gas supplied to an external loop or an output can be controlled by adjusting the rotational speed of the second valve member, for example.

In implementations, the second valve member may be configured to connect to the pressurized gas in the first orientation for charging the external loop and/or the second orientation for supplying the second fluid from the external loop to the output. For example, the first valve member may include one or more (e.g., three) channel legs extending radially from a port of the first valve member adjacent the second valve member. The one or more channel legs are configured to connect a channel of the second valve member to the pressurized gas. The second valve member may be configured to connect to the external loop and/or the output in a third orientation (e.g., rotational position) between the first and second orientations. This third orientation may be at, for example, a half-way point between the other two orientations. In implementations, a valve member (e.g., a stator) for a valve assembly may also include an additional connection to a port connected to the output. For example, the additional connection may comprise a port positioned in the side of the first valve member to furnish online dilution of, for example, a sample delivered to a nebulizer. This configuration can be used to provide a high flow rate of sample and diluent with a lower sample flow rate, while preventing diffusion between the sample and the carrier fluid at the back of a sample loop. In the following discussion, example implementations of valve assemblies are described.

Example Implementations

Figure 1:
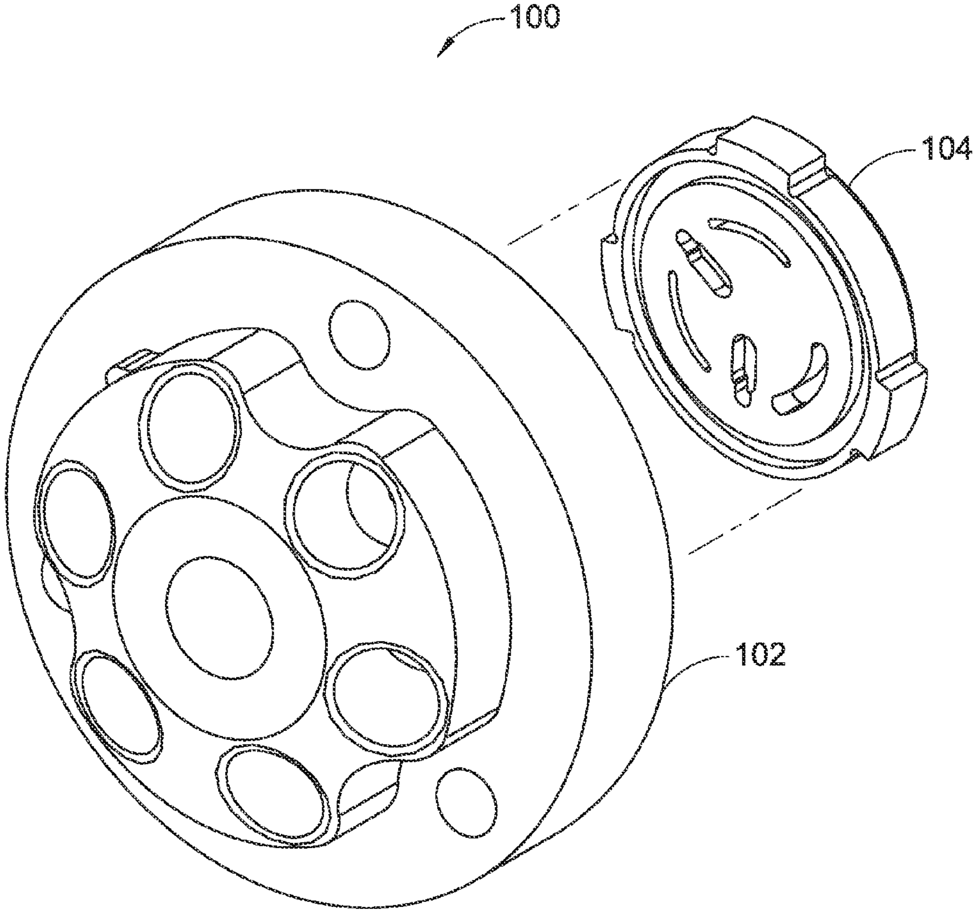
FIG. 1 is an exploded isometric view illustrating a stator and a rotor for a multiport flow valve configured to provide a half-way burst of gas in accordance with example implementations of the present disclosure.
Figure 2A:
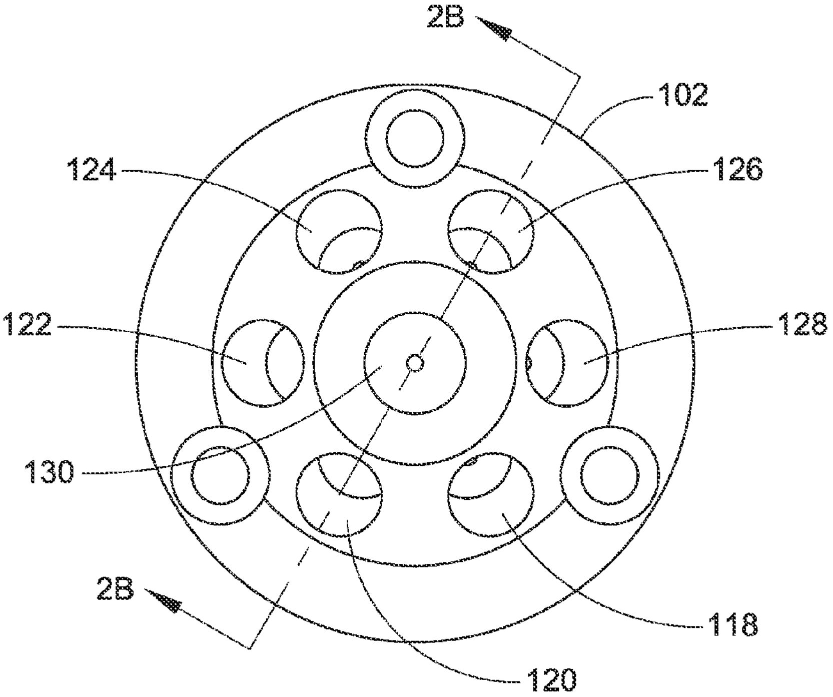
FIG. 2A is a top plan view of a multiport flow valve stator head with a center bypass port configured to provide a half-way burst of gas in accordance with example implementations of the present disclosure.
Figure 2B:
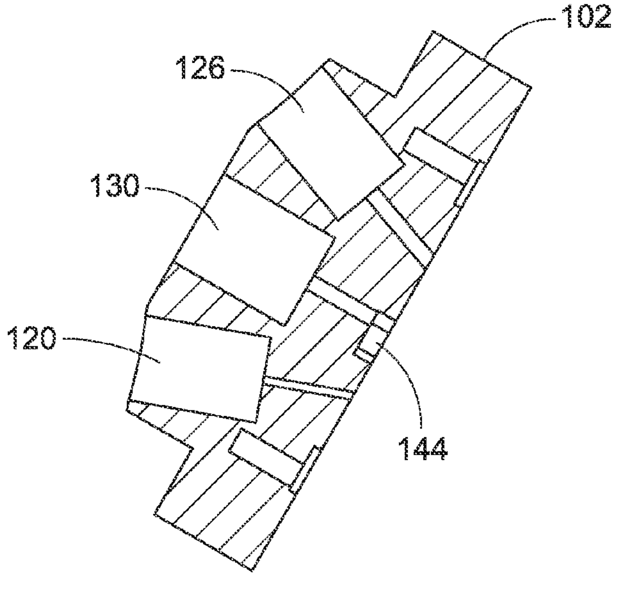
FIG. 2B is a partial cross-sectional side elevation view of the stator head illustrated in FIG. 2A.
Figure 2C:
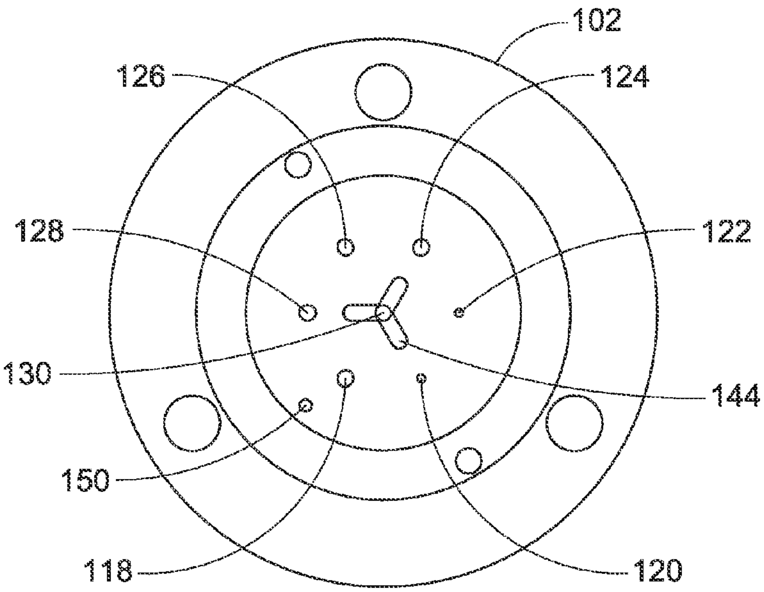
FIG. 2C is a bottom plan view of the stator head illustrated in FIG. 2A.
Figure 2D:
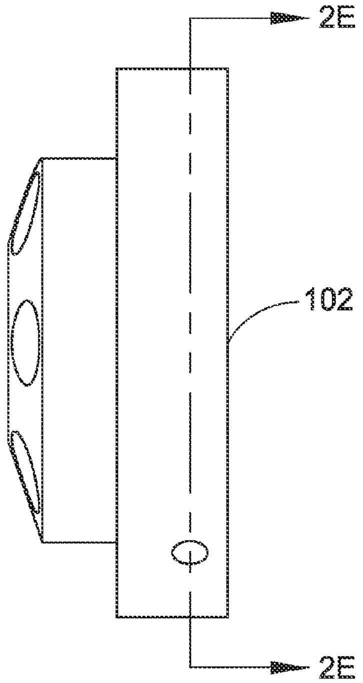
FIG. 2D is a side elevation view of the stator head illustrated in FIG. 2A.
Figure 2E:
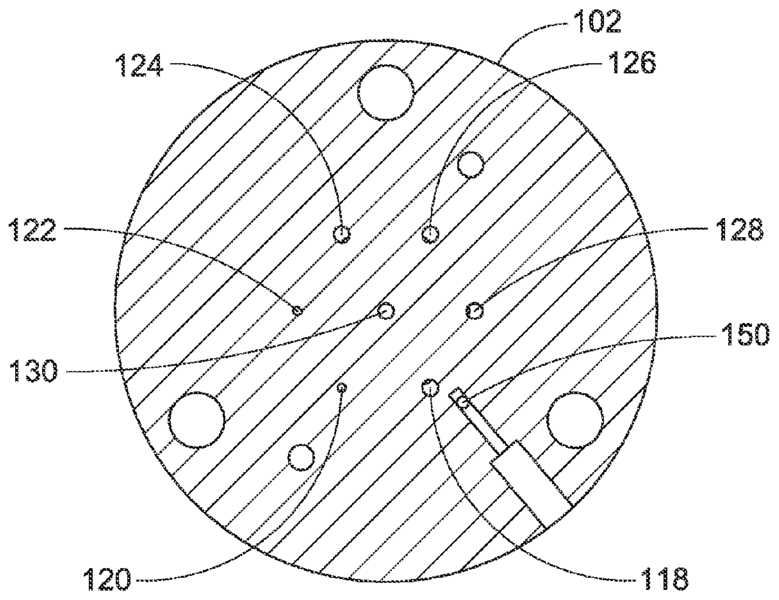
FIG. 2E is a partial cross-sectional top plan view of the stator head illustrated in FIG. 2A.
Figure 2F:
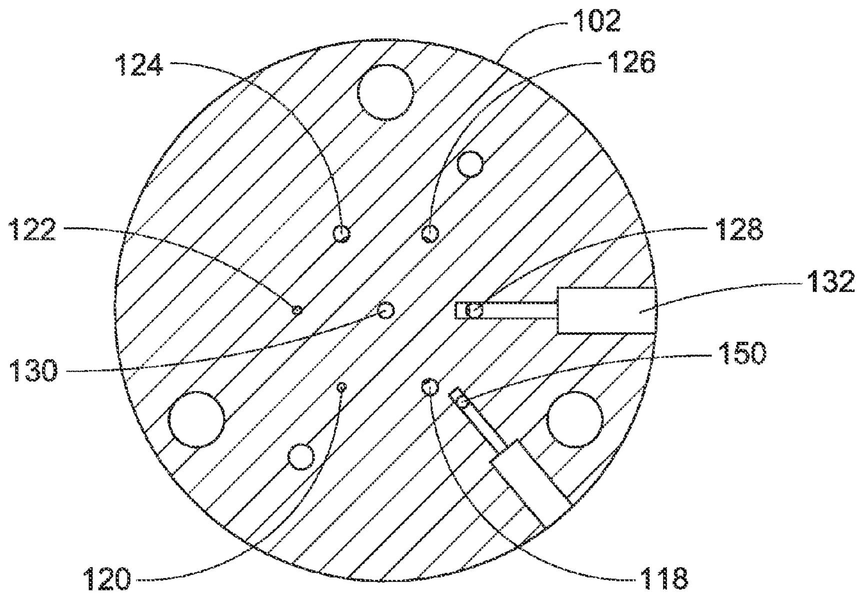
FIG. 2F is a partial cross-sectional top plan view of a multiport flow valve stator head with a center bypass port configured to provide a half-way burst of gas, and a side port configured to supply a diluent to provide online dilution in accordance with example implementations of the present disclosure.
Figure 3A:
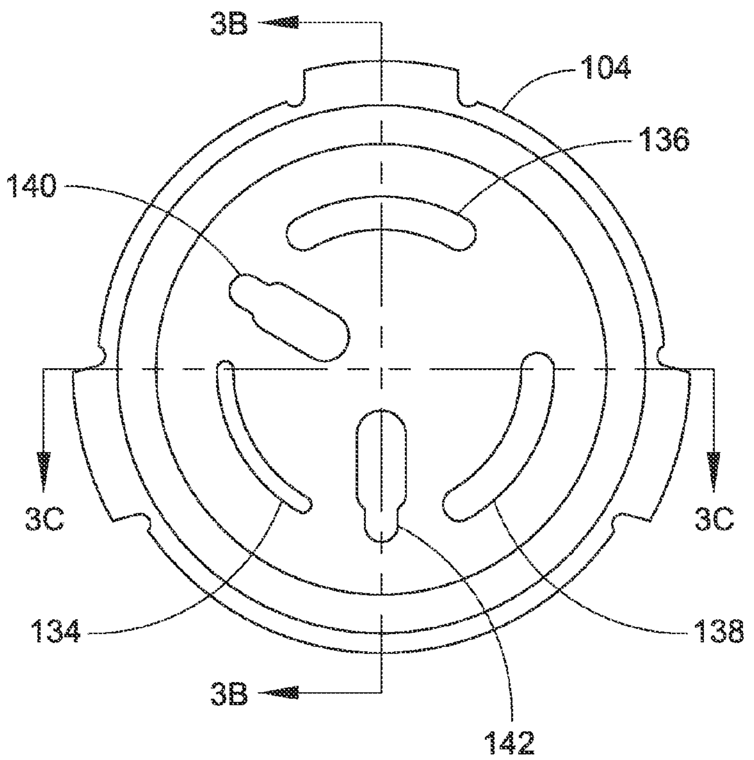
FIG. 3A is a top plan view of a rotor for a multiport flow valve with a center bypass port configured to provide a half-way burst of gas in accordance with example implementations of the present disclosure.
Figure 3B:
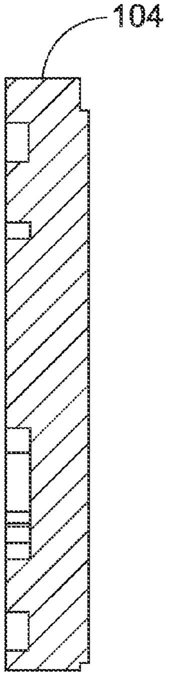
FIG. 3B is a partial cross-sectional side elevation view of the rotor illustrated in FIG. 3A.
Figure 3C:
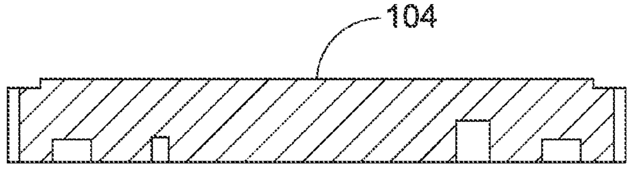
FIG. 3C is another partial cross-sectional side elevation view of the rotor illustrated in FIG. 3A.

FIGS. 1 through 3 illustrate an example stator 102 and an example rotor 104 for a valve assembly 100. The valve assembly 100 includes a first valve member and a second valve member coupled adjacent the first valve member. As shown, the valve assembly 100 can be configured as a rotary valve assembly having a first valve member comprising a stator 102 and a second valve member comprising a rotor 104 coupled adjacent the stator 102 so that it may rotate with respect to the stator 102. The valve assembly 100 is configured to provide a burst of gas (e.g., a bubble) to equipment connected thereto. In implementations, each bubble can be as small as about one to two microliters (1-2 μL) in volume. The valve assembly 100 can furnish separation between two fluids (e.g., a sample fluid and a carrier fluid) supplied to instrumentation, such as ICP spectrometry instrumentation, and so forth. It should be noted that while the accompanying figures show the stator 102 and the rotor 104 of the valve assembly 100, the valve assembly 100 may also include additional components, such as components for holding the rotor 104 adjacent the stator 102, and so forth. For example, the valve assembly 100 may further include a drive configured to rotate the rotor 104 and/or the stator 102, and a housing configured to support the stator 102 and/or the rotor 104 adjacent the stator 102.

The stator 102 includes ports configured to connect to an external loop (e.g., sample loop 106), an output (e.g., nebulizer 108), and a vent/waste 110. The stator 102 is configured to receive a first fluid (e.g., a carrier fluid 112), a second fluid (e.g., a sample fluid 114), and a pressurized gas 116. In implementations, the pressurized gas 116 may comprise an inert gas, such as argon, nitrogen, and so forth. In some instances, the pressurized gas 116 may be pressurized to between about fifteen to twenty pounds per square inch (15-20 psi); however, this range is provided by way of example only and is not meant to be restrictive of the present disclosure. The stator 102 may include a first port 118 configured to connect to the sample loop 106, a second port 120 configured to receive the carrier fluid 112, a third port 122 configured to connect to the nebulizer 108, a fourth port 124 configured to connect to the sample loop 106, a fifth port 126 configured to receive the sample fluid 114, a sixth port 128 configured to connect to waste 110, and a seventh port 130 configured to receive the pressurized gas 116. In implementations, the stator 102 may also include an eighth port 132 (e.g., as shown in FIG. 2F) configured to connect to the nebulizer 108. The eighth port 132 may be positioned in the side of the stator 102 to furnish online dilution of, for example, the sample fluid 114. For instance, a source of diluent can be connected to the eighth port 132, and the diluent can be supplied while the sample fluid 114 is pumped to the nebulizer 108. The eighth port 132 may also be used to provide a rinse for rinsing the connection to the nebulizer 108. In implementations, the stator 102 may also include a drain port 150, which may be connected to a channel in the rotor 104. In implementations, fluid flow to the ports of the stator 102 can be controlled using an instrument such as a valve controller (not shown).

Figure 4A:
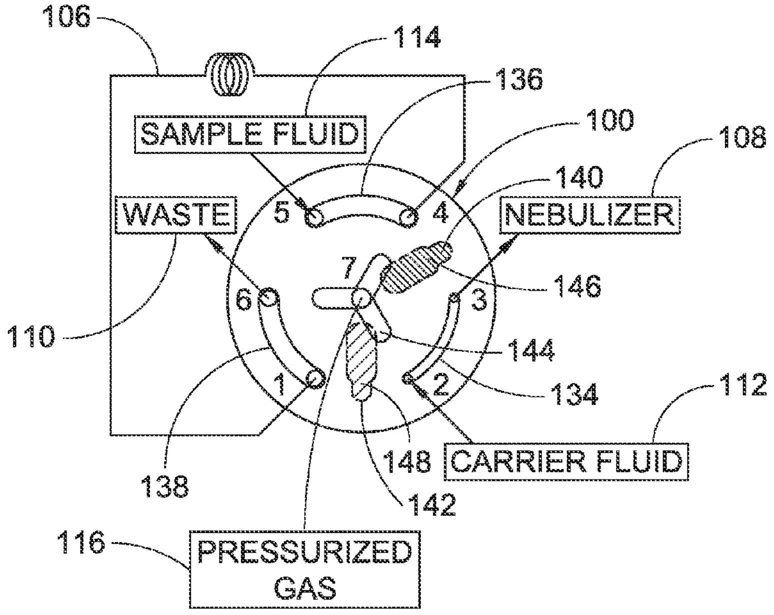
FIG. 4A is a diagrammatic view illustrating a multiport flow valve configured to provide a half-way burst of gas, where the multiport flow valve is shown in a load configuration in accordance with example implementations of the present disclosure.
Figure 4B:
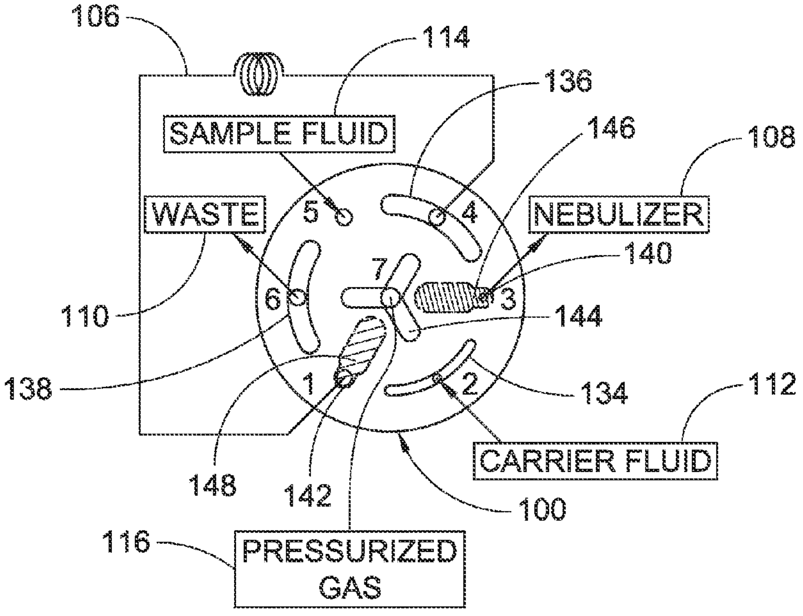
FIG. 4B is a diagrammatic view of the multiport flow valve illustrated in FIG. 4A, where the multiport flow valve is shown in a half-way configuration in accordance with example implementations of the present disclosure.
Figure 4C:
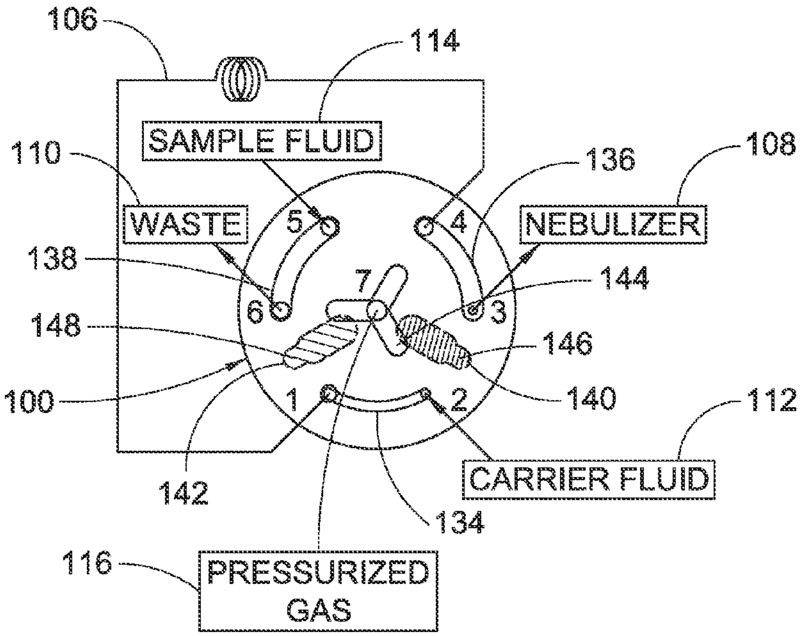
FIG. 4C is a diagrammatic view of the multiport flow valve illustrated in FIG. 4A, where the multiport flow valve is shown in an inject configuration in accordance with example implementations of the present disclosure.

The rotor 104 includes channels configured to connect the sample loop 106 to the sample fluid 114 in a first (load) orientation for charging the sample loop 106 with the sample fluid 114 (e.g., as shown in FIG. 4A), and to connect the sample loop 106 to the nebulizer 108 in a second (inject) orientation for supplying the sample fluid 114 from the sample loop 106 to the nebulizer 108 (e.g., as shown in FIG. 4C). For example, the rotor 104 may include a first channel 134 configured to connect the second port 120 to the third port 122 in the first orientation for charging the sample loop 106 with the sample fluid 114, and to connect the first port 118 to the second port 120 in the second orientation for supplying the sample fluid 114 from the sample loop 106 to the nebulizer 108. The rotor 104 may also include a second channel 136 configured to connect the fourth port 124 to the fifth port 126 in the first orientation, and to connect the third port 122 to the fourth port 124 in the second orientation. The rotor 104 may further include a third channel 138 configured to connect the sixth port 128 to the first port 118 in the first orientation, and to connect the fifth port 126 to the sixth port 128 in the second orientation for supplying the sample fluid 114 from the sample loop 106 to the nebulizer 108.

Figure 4D:
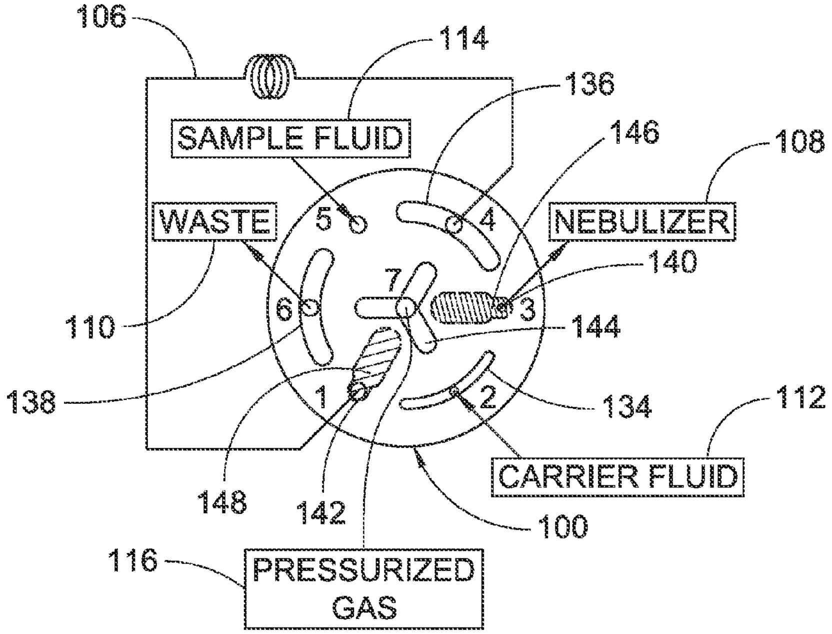
FIG. 4D is a diagrammatic view of the multiport flow valve illustrated in FIG. 4A, where the multiport flow valve is shown in a half-way configuration in accordance with example implementations of the present disclosure.

The rotor 104 also includes one or more additional channels configured to connect to the pressurized gas 116 in the first orientation and/or the second orientation for receiving the pressurized gas 116. The one or more channels are configured to connect to the sample loop 106 and/or the nebulizer 108 in a third orientation between the first orientation and the second orientation for supplying a burst of the pressurized gas 116 (e.g., a bubble) to the sample loop 106 and/or the nebulizer 108. For example, the rotor 104 may be configured to connect the one or more channels to the sample loop 106 and/or the nebulizer 108 in a position half-way between the first and second orientations (e.g., as shown in FIGS. 4B and 4D). In implementations, the rotor 104 can include a fourth channel 140 for connecting to the seventh port 130 in the first orientation and/or the second orientation for receiving the pressurized gas 116, and for connecting to the third port 122 in the third orientation between the first and second orientations for supplying the pressurized gas 116 to the nebulizer 108. Further, the rotor 104 can include a fifth channel 142 for connecting to the seventh port 130 in the first orientation and/or the second orientation for receiving the pressurized gas 116, and for connecting to the first port 118 in the third orientation between the first and second orientations for supplying the pressurized gas 116 to, for instance, the back of the sample loop 106.

Figure 5:
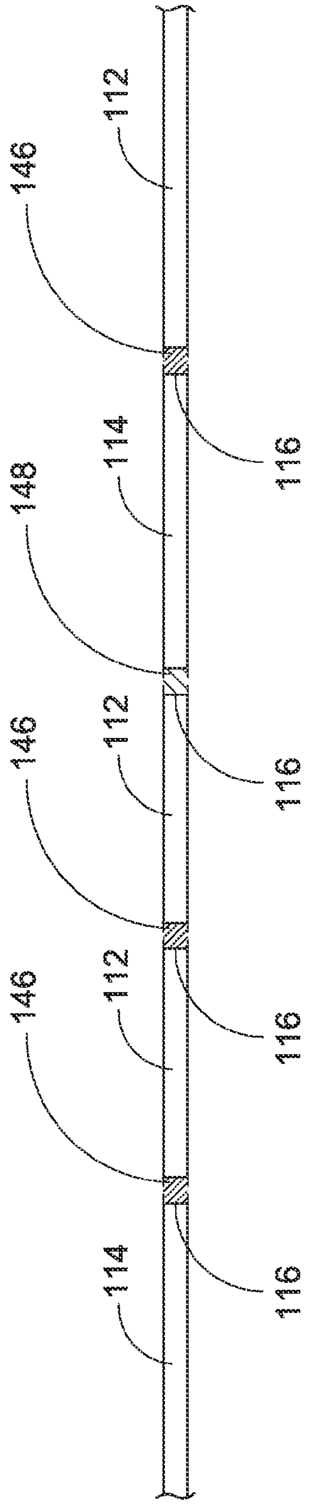
FIG. 5 is a diagrammatic illustration of flow from a multiport flow valve to a nebulizer, where the multiport flow valve is furnished with a center bypass port configured to provide one or more half-way bursts of gas in accordance with example implementations of the present disclosure.

In implementations, the stator 102 may include one or more channels (e.g., channel legs 144) configured to connect to the fourth channel 140 and/or the fifth channel 142 of the rotor 104 in the first orientation and/or the second orientation. The channel legs 144 are configured to connect the fourth channel 140 and/or the fifth channel 142 of the rotor 104 to the pressurized gas 116 (e.g., via the seventh port 130). For example, the stator 102 may include a three-legged channel connected to the seventh port 130, where the legs 144 extend radially adjacent the rotor 104. A bubble/first bust of gas 146 may be supplied to the nebulizer 108 from one of the legs 144 of the seventh port 130 via the fourth channel 140, while a bubble/second burst of gas 148 may be supplied to the nebulizer from another of the legs 144 of the seventh port 130 via the fifth channel 142 between the sample fluid 114 and the carrier fluid 112, at, for instance, the back of the sample loop 106. In this manner, the valve assembly 100 can be configured to provide multiple bursts of gas to equipment connected to the valve assembly 100 as the valve assembly 100 is actuated to load and inject the sample fluid 114. This provides separation between the sample fluid 114 and the carrier fluid 112 (e.g., as shown in FIG. 5).

Referring now to FIG. 7, this separation can provide a signal 700 having a substantially flat profile (e.g., as opposed to a signal 702 resulting from mixing between sample fluid and carrier fluid). Thus, the valve assembly 100 of the present disclosure can be used to provide a high flow rate of sample and diluent with a lower sample flow rate, which can be between, but not necessarily limited to: about five to one hundred microliters (5-100 μL) (e.g., depending upon loop size, and so forth). Further, this configuration can prevent diffusion between the sample fluid 114 and the carrier fluid 112 without adding large quantities of gas between the sample fluid and the carrier fluid that could add instability to the sample stream and the resulting signal.

It should be noted that while the terms "stator" and "rotor" are used herein to describe the first and second valve members, these terms are provided by way of example only (e.g., to illustrate how these components interface (e.g., rotate) with respect to one another), and are not meant to limit how the valve members can be actuated with respect to an external reference (e.g., valve mounting hardware, or the like). Thus, in one particular example, a component described as a "stator" may remain substantially stationary (e.g., with respect to an external reference, such as valve mounting hardware), and a component described as a "rotor" may rotate with respect to the stator. However, in another particular example, a component described as a "stator" may rotate with respect to a rotor, and a component described as a "rotor" may remain substantially stationary (e.g., with respect to valve mounting hardware). Further, in some implementations, both a component described as a "stator" and a component described as a "rotor" may rotate with respect to an external reference. Further, the fourth channel 140 and/or the fifth channel 142 of the rotor 104 may be connected to other ports of the stator 102 in the first orientation and/or the second orientation.

Example Procedures

Figure 6:
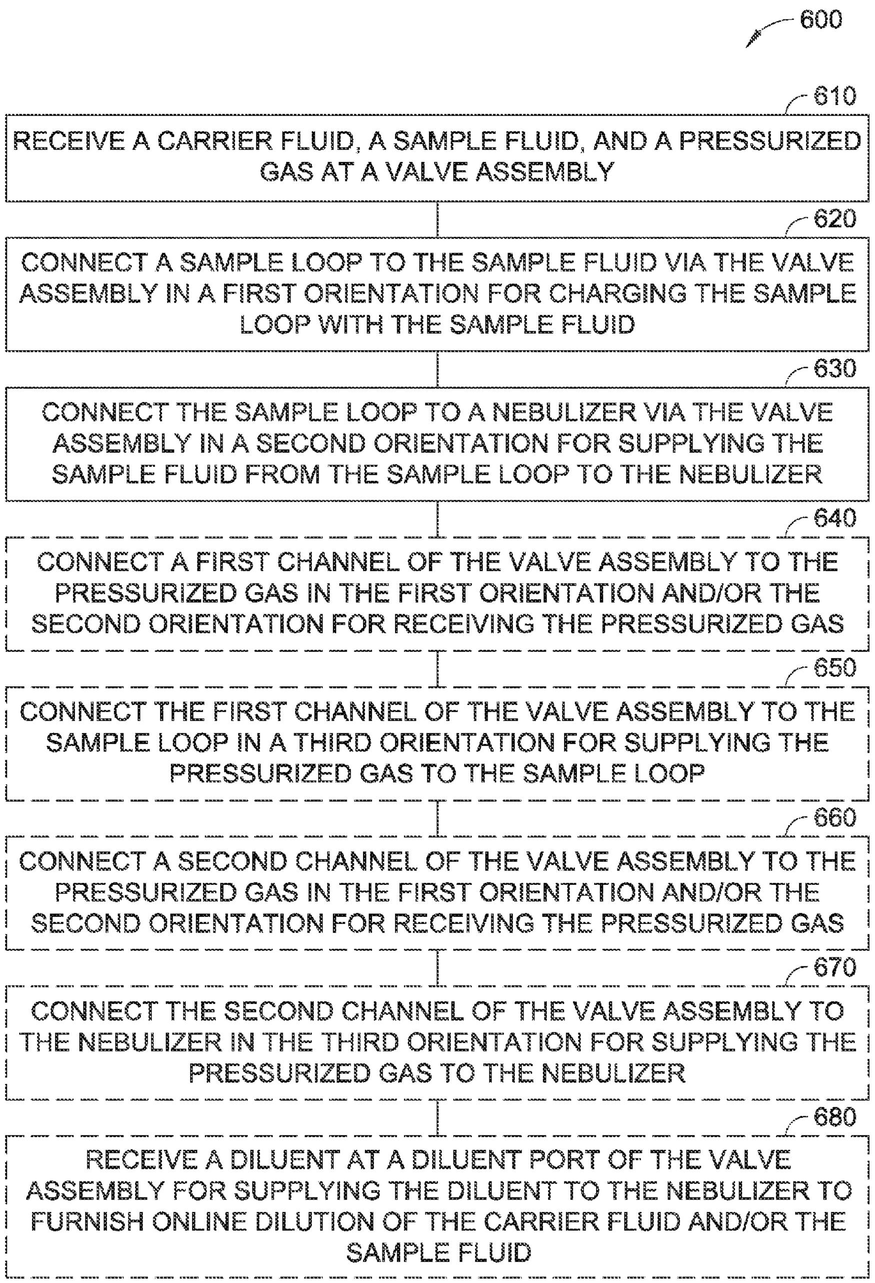
FIG. 6 is a flow diagram illustrating a method for providing a half-way burst of gas in accordance with example implementations of the present disclosure.

Referring now to FIG. 6, example techniques for injecting a burst of gas (e.g., a bubble) into a fluid stream between two fluids (e.g., a carrier fluid and a sample fluid) are described.

FIG. 6 depicts a process 600, in an example implementation, for injecting a burst of gas (e.g., a bubble) into a fluid stream between two fluids using, for example, the valve assembly 100 illustrated in FIGS. 1 through 4 and described above. In the process 600 illustrated, a carrier fluid, a sample fluid, and a pressurized gas are received at a valve assembly (Block 610). For example, with reference to FIGS. 1 through 4, stator 102 of valve assembly 100 is configured to receive carrier fluid 112, sample fluid 114, and pressurized gas 116.

Then, a sample loop can be connected to the sample fluid via the valve assembly in a first orientation for charging the sample loop with the sample fluid (Block 620). For example, with continuing reference to FIGS. 1 through 4, first port 118 and fourth port 124 of stator 102 are configured to connect to sample loop 106, and fifth port 126 of stator 102 is configured to receive sample fluid 114. Further, rotor 104 includes second channel 136 configured to connect fourth port 124 to fifth port 126 for charging sample loop 106 with sample fluid 114 (e.g., as shown in FIG. 4A).

Next, the sample loop can be connected to a nebulizer via the valve assembly in a second orientation for supplying the sample fluid from the sample loop to the nebulizer (Block 630). For example, with continuing reference to FIGS. 1 through 4, third port 122 of stator 102 is configured to connect to nebulizer 108. Further, second channel 136 of rotor 104 is configured to connect third port 122 of stator 102 to fourth port 124 for supplying sample fluid 114 from sample loop 106 to nebulizer 108 (e.g., as shown in FIG. 4C).

In implementations, a first channel of the valve assembly may be connected to the pressurized gas in the first orientation and/or the second orientation for receiving the pressurized gas (Block 640). For example, with continuing reference to FIGS. 1 through 4, seventh port 130 of stator 102 is configured to receive pressurized gas 116, and rotor 104 includes fifth channel 142 for connecting to seventh port 130 in the first orientation and/or the second orientation of rotor 104 for receiving pressurized gas 116. Then, the first channel of the valve assembly may be connected to the sample loop in a third orientation for supplying the pressurized gas to the sample loop (Block 650). For example, with continuing reference to FIGS. 1 through 4, fifth channel 142 connects to first port 118 in a half-way orientation between the first and second orientations for supplying the pressurized gas 116 to sample loop 106.

Further, a second channel of the valve assembly may be connected to the pressurized gas in the first orientation and/or the second orientation for receiving the pressurized gas (Block 660). For example, with continuing reference to FIGS. 1 through 4, rotor 104 includes fourth channel 140 for connecting to seventh port 130 in the first orientation and/or the second orientation of rotor 104 for receiving pressurized gas 116. Next, the second channel of the valve assembly may be connected to the nebulizer in the third orientation for supplying the pressurized gas to the nebulizer (Block 670). For example, with continuing reference to FIGS. 1 through 4, fourth channel 140 connects to third port 122 in a half-way orientation for supplying pressurized gas 116 to nebulizer 108.

In some implementations, a diluent may be received at a diluent port of the valve assembly for supplying the diluent to the nebulizer to furnish online dilution of the carrier fluid and/or the sample fluid (Block 680). For example, with continuing reference to FIGS. 1 through 4, stator 102 includes eighth port 132 configured to connect to nebulizer 108. Further, eighth port 132 may be positioned in the side of stator 102 to furnish online dilution of, for example, sample fluid 114.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A valve assembly comprising:

a first valve member having a first plurality of ports configured to connect to an external loop, an output, and a vent and a second plurality of ports configured to receive a first fluid, a second fluid, and a pressurized gas; and a second valve member coupled adjacent the first valve member, the second valve member having a plurality of channels configured to connect the external loop to the second fluid in a first orientation for charging the external loop with the second fluid and to connect the external loop to the output in a second orientation for supplying the second fluid from the external loop to the output, and a channel configured to connect to the pressurized gas in at least one of the first orientation or the second orientation for receiving a portion of the pressurized gas and to connect to at least one of the external loop or the output in a third orientation between the first orientation and the second orientation for supplying the portion of the pressurized gas to the at least one of the external loop or the output.

2. The valve assembly as recited in claim 1, wherein the first valve member comprises a stator and the second valve member comprises a rotor coupled adjacent the stator.

3. The valve assembly as recited in claim 1, wherein the external loop comprises a sample loop, the output comprises a nebulizer, the first fluid comprises a carrier fluid, and the second fluid comprises a sample fluid.

4. The valve assembly as recited in claim 1, wherein the first valve member comprises a channel leg configured to connect to the channel of the second valve member in the at least one of the first orientation or the second orientation to connect the channel to the pressurized gas.

5. The valve assembly as recited in claim 1, wherein the second valve member further comprises a second channel configured to connect to the pressurized gas in at least one of the first orientation or the second orientation for receiving a second portion of the pressurized gas and to connect to the other of the at least one of the external loop or the output in the third orientation for supplying the second portion of the pressurized gas to the other of the at least one of the external loop or the output.

6. The valve assembly as recited in claim 5, wherein the first valve member comprises a three-legged channel configured to connect to the channel of the second valve member and the second channel of the second valve member in the at least one of the first orientation or the second orientation to connect the channel of the second valve member and the second channel of the second valve member to the pressurized gas.

7. The valve assembly as recited in claim 6, wherein each leg of the three-legged channel extends radially adjacent the second valve member.

8. The valve assembly as recited in claim 1, wherein the first valve member further comprises a port connected to one of the first plurality of ports connected to the output to furnish online dilution of at least one of the first fluid or the second fluid.

9. A valve assembly comprising:

a first valve member having a first port configured to connect to an external loop, a second port configured to receive a first fluid, a third port configured to connect to an output, a fourth port configured to connect to the external loop, a fifth port configured to receive a second fluid, a sixth port configured to connect to a vent, and a seventh port configured to receive a pressurized gas; and a second valve member coupled adjacent the first valve member, the second valve member having a first channel configured to connect the second port to the third port in a first orientation for charging the external loop with the second fluid and to connect the first port to the second port in a second orientation for supplying the second fluid from the external loop to the output, a second channel configured to connect the fourth port to the fifth port in the first orientation and to connect the third port to the fourth port in the second orientation, a third channel configured to connect the sixth port to the first port in the first orientation and to connect the fifth port to the sixth port in the second orientation, and a fourth channel configured to connect to the seventh port in at least one of the first orientation or the second orientation for receiving a portion of the pressurized gas and to connect to at least one of the first port or the third port in a third orientation between the first orientation and the second orientation for supplying the portion of the pressurized gas to at least one of the external loop or the output.

10. The valve assembly as recited in claim 9, wherein the first valve member comprises a stator and the second valve member comprises a rotor coupled adjacent the stator.

11. The valve assembly as recited in claim 9, wherein the external loop comprises a sample loop, the output comprises a nebulizer, the first fluid comprises a carrier fluid, and the second fluid comprises a sample fluid.

12. The valve assembly as recited in claim 9, wherein the first valve member comprises a channel leg configured to connect to the fourth channel of the second valve member in the at least one of the first orientation or the second orientation to connect the fourth channel to the seventh port of the first valve member.

13. The valve assembly as recited in claim 9, wherein the second valve member further comprises a fifth channel configured to connect to the seventh port in at least one of the first orientation or the second orientation for receiving a second portion of the pressurized gas and to connect to the other of the at least one of the first port or the third port in the third orientation for supplying the second portion of the pressurized gas to the other of the at least one of the external loop or the output.

14. The valve assembly as recited in claim 13, wherein the first valve member comprises a three-legged channel configured to connect to the fourth channel of the second valve member and the fifth channel of the second valve member in the at least one of the first orientation or the second orientation to connect the fourth channel of the second valve member and the fifth channel of the second valve member to the seventh port of the first valve member.

15. The valve assembly as recited in claim 14, wherein each leg of the three-legged channel extends radially adjacent the second valve member.

16. The valve assembly as recited in claim 9, wherein the first valve member further comprises an eighth port connected to the third port to furnish online dilution of at least one of the first fluid or the second fluid.

17. A method comprising:

receiving a carrier fluid, a sample fluid, and a pressurized gas at a valve assembly;

connecting a sample loop to the sample fluid via the valve assembly in a first orientation for charging the sample loop with the sample fluid;

connecting the sample loop to a nebulizer via the valve assembly in a second orientation for supplying the sample fluid from the sample loop to the nebulizer;

connecting a channel of the valve assembly to the pressurized gas in at least one of the first orientation or the second orientation for receiving a portion of the pressurized gas; and connecting the channel of the valve assembly to at least one of the sample loop or the nebulizer in a third orientation between the first orientation and the second orientation for supplying the portion of the pressurized gas to the at least one of the sample loop or the nebulizer.

18. The method as recited in claim 17, further comprising:

connecting a second channel of the valve assembly to the pressurized gas in at least one of the first orientation or the second orientation for receiving a second portion of the pressurized gas; and connecting the second channel of the valve assembly to the other of the at least one of the sample loop or the nebulizer in the third orientation for supplying the second portion of the pressurized gas to the other of the at least one of the sample loop or the nebulizer.

19. The method as recited in claim 18, wherein the valve assembly comprises a three-legged channel configured to connect to the channel of the valve assembly and the second channel of the valve assembly in the at least one of the first orientation or the second orientation to connect the channel of the valve assembly and the second channel of the valve assembly to the pressurized gas.

20. The method as recited in claim 17, further comprising receiving a diluent at a diluent port of the valve assembly for supplying the diluent to the nebulizer to furnish online dilution of at least one of the carrier fluid or the sample fluid.

* * * * *